United States Patent
Blurton

(10) Patent No.: US 9,615,953 B2
(45) Date of Patent: Apr. 11, 2017

(54) METHOD, APPARATUS AND SYSTEM FOR PREVENTING OR REDUCING THE SEVERITY OF HEMORRHOIDS

(71) Applicant: Stetrix, Inc., Oakland, TN (US)

(72) Inventor: David D. Blurton, Whiteville, TN (US)

(73) Assignee: STETRIX, INC., Oakland, TN (US)

( * ) Notice: Subject to any disclaimer, the term of this patent is extended or adjusted under 35 U.S.C. 154(b) by 246 days.

(21) Appl. No.: 14/252,480

(22) Filed: Apr. 14, 2014

(65) Prior Publication Data

US 2014/0222017 A1 Aug. 7, 2014

Related U.S. Application Data

(60) Continuation of application No. 13/404,891, filed on Feb. 24, 2012, now abandoned, which is a division of
(Continued)

(51) Int. Cl.
*A61B 17/42* (2006.01)
*A61F 5/00* (2006.01)

(52) U.S. Cl.
CPC ............ *A61F 5/0093* (2013.01); *A61B 17/42* (2013.01)

(58) Field of Classification Search
CPC ...... A61B 17/42; A61F 5/0093; A61F 2/0004; A61F 2/0009; A61F 6/08; A61H 19/00; A61H 21/00; A61D 9/02
(Continued)

(56) References Cited

U.S. PATENT DOCUMENTS

| 1,511 | A | | 3/1840 | Truss |
| 96,460 | A | * | 11/1869 | Mervine, Jr. ......... A61F 5/0093 |
| | | | | 128/98.1 |

(Continued)

FOREIGN PATENT DOCUMENTS

| GB | 512161 A | * | 8/1939 | ........... A61F 5/0093 |
| GB | 512161 A | | 8/1939 | |

(Continued)

OTHER PUBLICATIONS

Abramowitz et al., "Epidemiology of anal lesions (fissure and thrombosed external hemorroid) during pregnancy and post-partum", Gynecol Obstet Fertil 2003, No. 31, 546-549.
(Continued)

*Primary Examiner* — David C Eastwood
(74) *Attorney, Agent, or Firm* — Haynes and Boone, LLP

(57) ABSTRACT

Described herein is a device, comprising a base and a positioning member, for preventing or reducing the severity of external hemorrhoids in a patient during childbirth. The base has a first longitudinal axis and a surface extending from a first side of the base in a first direction corresponding to a height of the surface, which has a second longitudinal axis with a constant angular orientation relative to the first longitudinal axis, is of a size greater than the anal orifice, is anatomically configured to contact only the perianal region and to not substantially enter the anal canal or substantially interfere with the birthing canal. The positioning member extends from a second side of the base in a second direction away from the first side, and includes a substantially rigid structure configured for gripping by a user to position and hold the device against the anal orifice.

37 Claims, 13 Drawing Sheets

Related U.S. Application Data application No. 11/197,627, filed on Aug. 5, 2005, now Pat. No. 8,123,760.

(58) Field of Classification Search
USPC .... 606/119, 197, 1, 201, 204, 121; 600/197, 600/29–41; 128/830, 834–835, 842, 897, 128/98.1, 99.1
See application file for complete search history.

(56) References Cited

U.S. PATENT DOCUMENTS

| | | | |
|---|---|---|---|
| 142,972 A | 9/1873 | West | |
| 316,903 A | 4/1885 | Lytle | |
| 453,880 A | 6/1891 | Coffee | |
| 655,618 A * | 8/1900 | Garver | A61F 5/0093 128/98.1 |
| 942,590 A | 12/1909 | Sanborn | |
| 969,134 A | 8/1910 | Cowie | |
| 1,249,195 A | 12/1917 | Raines | |
| 1,547,127 A | 2/1924 | Metzger | |
| 1,581,009 A | 4/1926 | McSherry | |
| 1,711,294 A | 4/1929 | Weitzner | |
| 1,877,766 A | 5/1931 | Kennedy | |
| 2,128,670 A | 8/1938 | Bolder | |
| 2,468,348 A | 4/1949 | Shore | |
| 2,615,445 A * | 10/1952 | Holmes | A61F 5/0093 128/107.1 |
| 2,653,599 A | 2/1953 | Bell | |
| 2,672,862 A * | 3/1954 | Krauss | A61F 5/0093 128/98.1 |
| 3,712,300 A | 1/1973 | Davidowitz | |
| 3,826,242 A | 7/1974 | Eggers | |
| 3,939,842 A | 2/1976 | Harris | |
| 3,985,125 A | 10/1976 | Rose | |
| 4,240,436 A | 12/1980 | Singleton | |
| 4,263,914 A | 4/1981 | Pawlak | |
| 4,365,631 A | 12/1982 | Kline | |
| 4,421,504 A | 12/1983 | Kline | |
| 4,432,351 A | 2/1984 | Hoary | |
| 4,439,180 A | 3/1984 | Kline | |
| 4,445,899 A | 5/1984 | Bond | |
| 4,484,919 A * | 11/1984 | Sohn | A61F 5/4401 604/358 |
| 4,583,542 A | 4/1986 | Boyd | |
| 4,638,806 A | 1/1987 | Bartlett | |
| 4,670,419 A | 6/1987 | Uda et al. | |
| 4,686,966 A | 8/1987 | Tsai | |
| 4,891,847 A | 1/1990 | Baker et al. | |
| 4,966,130 A | 10/1990 | Montaldi | |
| 5,072,720 A | 12/1991 | Francis et al. | |
| 5,178,627 A | 1/1993 | Hudock | |
| 5,179,937 A | 1/1993 | Lee | |
| 5,231,973 A | 8/1993 | Dickie | |
| 5,263,926 A | 11/1993 | Wilk | |
| 5,377,667 A | 1/1995 | Patton et al. | |
| 5,509,893 A | 4/1996 | Pracas | |
| 5,676,637 A | 10/1997 | Lee | |
| 5,695,484 A | 12/1997 | Cox | |
| 5,704,894 A | 1/1998 | Boutos | |
| 5,800,485 A | 9/1998 | Trop et al. | |
| 5,908,379 A | 6/1999 | Schaefer et al. | |
| 5,924,423 A | 7/1999 | Majlessi | |
| 5,935,595 A | 8/1999 | Steen | |
| 6,083,241 A | 7/2000 | Longo et al. | |
| 6,102,271 A | 8/2000 | Longo et al. | |
| 6,142,933 A | 11/2000 | Longo et al. | |
| D437,642 S | 2/2001 | Caballero | |
| 6,364,852 B1 | 4/2002 | Lee | |
| 6,428,004 B1 | 8/2002 | McQuitty et al. | |
| 6,503,192 B1 | 1/2003 | Ouchi | |
| 6,517,562 B1 | 2/2003 | Holland | |
| 6,537,132 B1 | 3/2003 | Alberts | |
| 6,627,632 B2 | 9/2003 | Parks et al. | |
| 6,712,841 B2 | 3/2004 | Gomez | |
| 6,716,229 B2 | 4/2004 | Toth | |
| 6,913,573 B1 | 7/2005 | Viscomi et al. | |
| 6,916,494 B2 | 7/2005 | Park | |
| 6,991,813 B2 | 1/2006 | Xu | |
| 7,160,294 B2 | 1/2007 | Croft | |
| 7,673,633 B2 | 3/2010 | Blurton et al. | |
| 7,766,931 B2 | 8/2010 | Blurton | |
| 8,062,277 B2 | 11/2011 | Fleming | |
| 8,123,760 B2 | 2/2012 | Blurton | |
| 8,277,427 B2 | 10/2012 | Edvardsen et al. | |
| 8,353,884 B2 | 1/2013 | Hansen et al. | |
| 2001/0000731 A1 | 5/2001 | Jia et al. | |
| 2001/0003157 A1 | 6/2001 | Toth | |
| 2002/0072522 A1 | 6/2002 | Parks et al. | |
| 2002/0142902 A1 | 10/2002 | Stein | |
| 2002/0147482 A1 | 10/2002 | Carter | |
| 2002/0187990 A1 | 12/2002 | Parks et al. | |
| 2002/0192273 A1 | 12/2002 | Buseman | |
| 2003/0021850 A1 | 1/2003 | Xu | |
| 2003/0229263 A1 | 12/2003 | Connors et al. | |
| 2003/0236442 A1 | 12/2003 | Connors et al. | |
| 2004/0076688 A1 | 4/2004 | Park | |
| 2004/0088031 A1 | 5/2004 | Gomez | |
| 2004/0217146 A1 | 11/2004 | Beck | |
| 2004/0254590 A1 | 12/2004 | Hoffman et al. | |
| 2005/0000003 A1 | 1/2005 | Bushelman | |
| 2005/0049660 A1 | 3/2005 | Croft | |
| 2005/0214327 A1 | 9/2005 | Brooks et al. | |
| 2006/0025766 A1 | 2/2006 | Heinrich et al. | |
| 2006/0144897 A1 | 7/2006 | Jankowski et al. | |
| 2006/0153927 A1 | 7/2006 | Xu | |
| 2006/0155340 A1 | 7/2006 | Schuler et al. | |
| 2006/0195146 A1 | 8/2006 | Tracey et al. | |
| 2006/0195153 A1 | 8/2006 | DiUbaldi et al. | |
| 2006/0198883 A1 | 9/2006 | Parks et al. | |
| 2007/0011802 A1 | 1/2007 | Holland | |

FOREIGN PATENT DOCUMENTS

| | | |
|---|---|---|
| GB | 1127548 A | 9/1968 |
| JP | 2007275309 | 10/1995 |
| JP | 2001129004 | 5/2001 |
| JP | 2001170093 | 6/2001 |
| WO | WO02/13680 A2 | 2/2002 |
| WO | WO03/053255 A1 | 7/2003 |

OTHER PUBLICATIONS

Danel, "Magnitude of Maternal Morbidity During Labor and Delivery: United States, 1993-1997", American Journal of Public Health, Apr. 2003, vol. 93, No. 4, , pp. 631-634.

http://www.thefreedictionary.com/ perineal, definition of the term perineal retrieved on Jan. 9, 2014.

International Search Report and Written Opinion of the International Searching Authority for PCT/US06/29583 dated Aug. 3, 2007.

Takano, Masahiro, "Anal Diseases Pregnancy and Parturition," 1990, Nippon Daicho Komonbyo Gakkai Zasshi, Tokyo, 1990; 43(6); pp. 1077-1082.

U.S. Appl. No. 11/197,627, filed Aug. 5, 2005; Final Office Action mailed Sep. 10, 2009, 17 pages.

U.S. Appl. No. 11/197,627, filed Aug. 5, 2005; Interview Summary mailed Nov. 3, 2009, 6 pages.

U.S. Appl. No. 11/197,627, filed Aug. 5, 2005; Amendment (with Affidavit) filed Nov. 10, 2009, in response to Final Office Action, 32 pages.

Frederick Francis Burghard, various authors, "A System of Operative Surgery, vol. IV (of 4)," Dec. 26, 2012 [Ebook #41710], www.gutenberg.org.

European Office Action dated Jul. 25, 2016 in connection with European Patent Application No. 06788889.1; 4 pp.

* cited by examiner

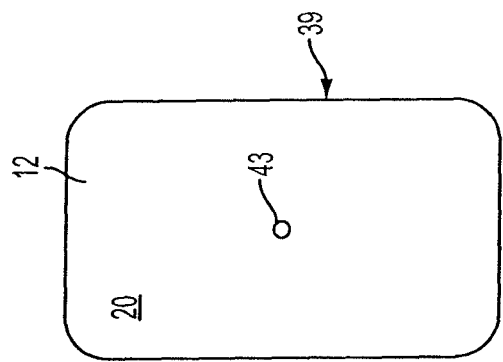
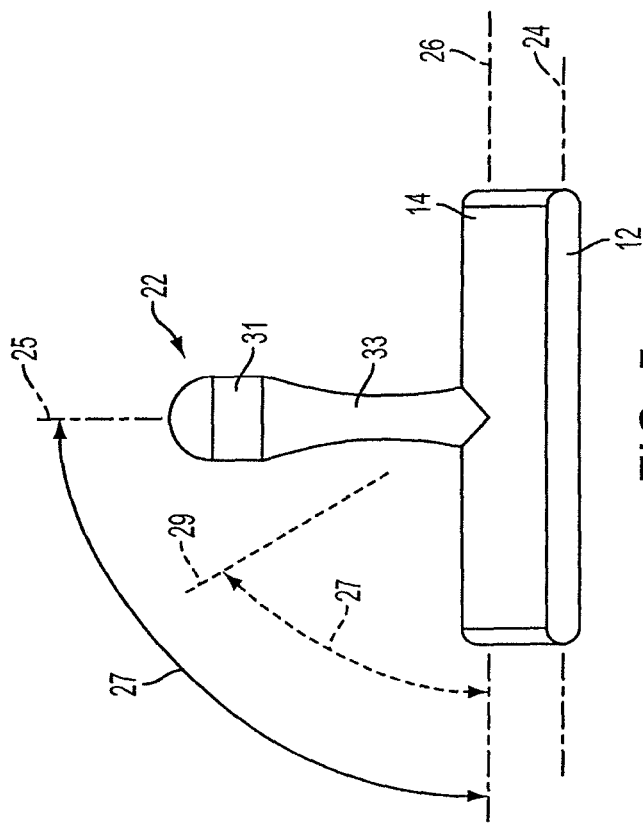

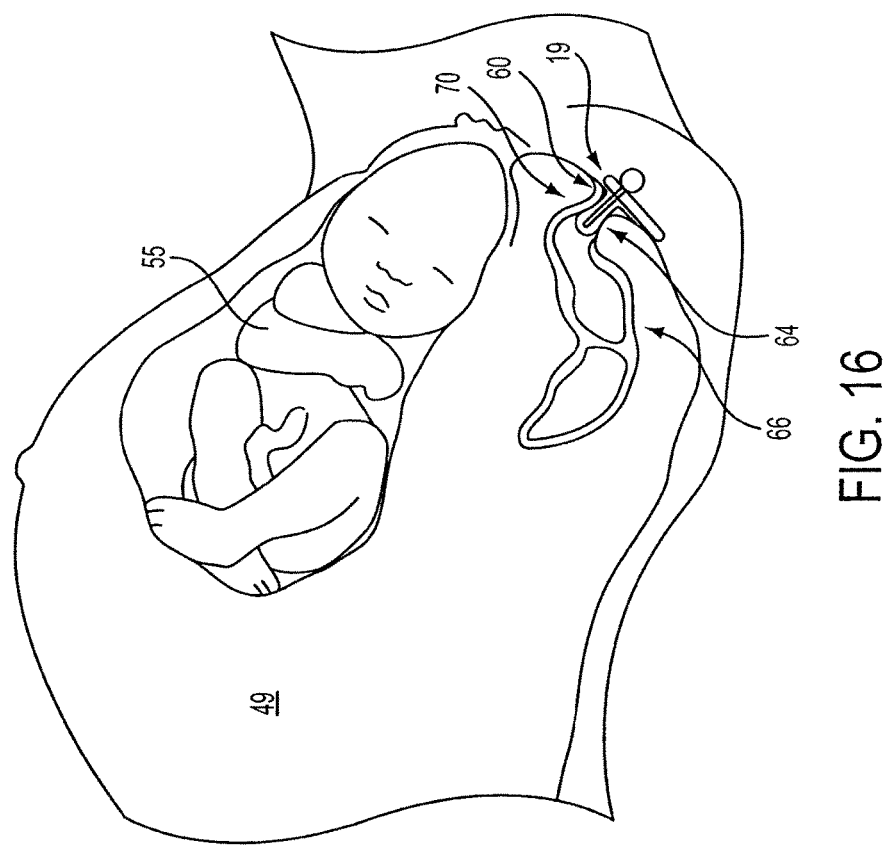

METHOD, APPARATUS AND SYSTEM FOR PREVENTING OR REDUCING THE SEVERITY OF HEMORRHOIDS

CROSS-REFERENCE TO RELATED APPLICATION

The present application is a continuation application of U.S. patent application Ser. No. 13/404,891, filed on Feb. 24, 2012, which claims priority to and the benefit of U.S. patent application Ser. No. 11/197,627, now U.S. Pat. No. 8,123,760, filed Aug. 5, 2005, each of which is hereby incorporated by reference in its entirety.

BACKGROUND

The disclosed embodiments relate to a method and apparatus for preventing or reducing the severity of hemorrhoids, and in particular, a method, apparatus, and system for preventing or reducing the severity of hemorrhoids during or immediately after labor or childbirth.

As many as 43% of women experience some type of obstetric complication during their childbirth hospitalization. Danel, American Journal of Public Health, 2003 93(4): 631-634. One of these labor and delivery-related complications is hemorrhoids, and in particular thrombosed external hemorrhoids (THE). It is reported that as many as 20-34% of pregnant women develop THE. Abramowitz, Gynecol Obstet Feral, 2003 31(6): 546-549.

In many countries, standard medical delivery positions, such as semi-sitting or dorsal lithotomy, require the patient to lie on her back. These standard medical delivery positions are believed to contribute to delivery-related hemorrhoids. These positions appear to increase intra-pelvic blood pressure when compared to other delivery positions, such as positions with the patient on hands and knees, or on the side, as in some Eastern countries. The reduction in pressure provided by non-supine or dorsal lithotomy delivery positions, however, appears to be enough to reduce the occurrence of THE. The primary reason obstetricians utilize these standard delivery positions, though, is because it places the patient in a preferred position for quickly performing emergency procedures, such as a Caesarian section. Thus, delivery-related hemorrhoids will persist as a complication in childbirths utilizing standard medical delivery positions.

Further, it is well known that mid-wives sometimes gently push on the anus or perianal area during crowning. This mild pressure often prevents the occurrence of THE. Unfortunately, to date, no one has developed a device for preventing or reducing hemorrhoids formed during or shortly after childbirth.

Additionally, some pharmaceutical companies have recently begun to look at this problem. So far they have been unable to address hemorrhoids caused by the labor and childbirth process because the same hormones that permit the elasticity of blood vessels in the anus are also responsible for the elasticity of tendons and joints, which is necessary for the birth process. Further, many physicians will be reluctant to prescribe any medication that is unnecessary during pregnancy.

Thus, new methods and apparatus are desired to prevent or reduce the severity of child delivery-related hemorrhoids.

BRIEF SUMMARY

In accordance with one aspect, the disclosed embodiments provide devices, methods, and systems for preventing or reducing the severity of external and/or internal hemorrhoids.

In one embodiment, a device for preventing or reducing the severity of internal and/or external hemorrhoids in a patient comprises a base and a raised portion connected to and extending in a first direction away from the base. The raised portion has a shape adapted to engage only a perianal region of the patient to apply pressure to an external rectal venous plexus.

In another embodiment, a method of preventing or reducing the severity of internal and/or external hemorrhoids in a patient comprises positioning a raised portion of a device in a pressure-inducing engagement position relative to only a perianal region of the patient to apply pressure to an external rectal venous plexus. The raised portion extending in a first direction away from a base. And, the method further includes securing the raised portion in the engagement position.

In another embodiment, a device for preventing or reducing the severity of internal and/or external hemorrhoids in a patient comprises a means for applying pressure to only a perianal region of the patient to apply pressure to an external rectal venous plexus. Further, the device comprises a means for securing the means for applying pressure to the patient to maintain engagement with the perianal region.

In yet another embodiment, the above-described devices and methods of treatment are applied before, during, or within 48 hours of childbirth.

Additional aspects and advantages of the disclosed embodiments are set forth in part in the description which follows, and in part are obvious from the description, or may be learned by practice of the disclosed embodiments. The aspects and advantages of the disclosed embodiments may also be realized and attained by the means of the instrumentalities and combinations particularly pointed out in the appended claims.

BRIEF DESCRIPTION OF THE DRAWINGS

The disclosed embodiments will hereinafter be described in conjunction with the appended drawings provided to illustrate and not to limit the disclosed embodiments, wherein like designations denote like elements, and in which:

FIG. 5 is a side view of the device of FIG. 3;

FIG. 6 is a bottom view of the device of FIG. 3;

FIG. 16 is a partial cross sectional view along line 16-16 of FIG. 15.

DETAILED DESCRIPTION

Figure 1:
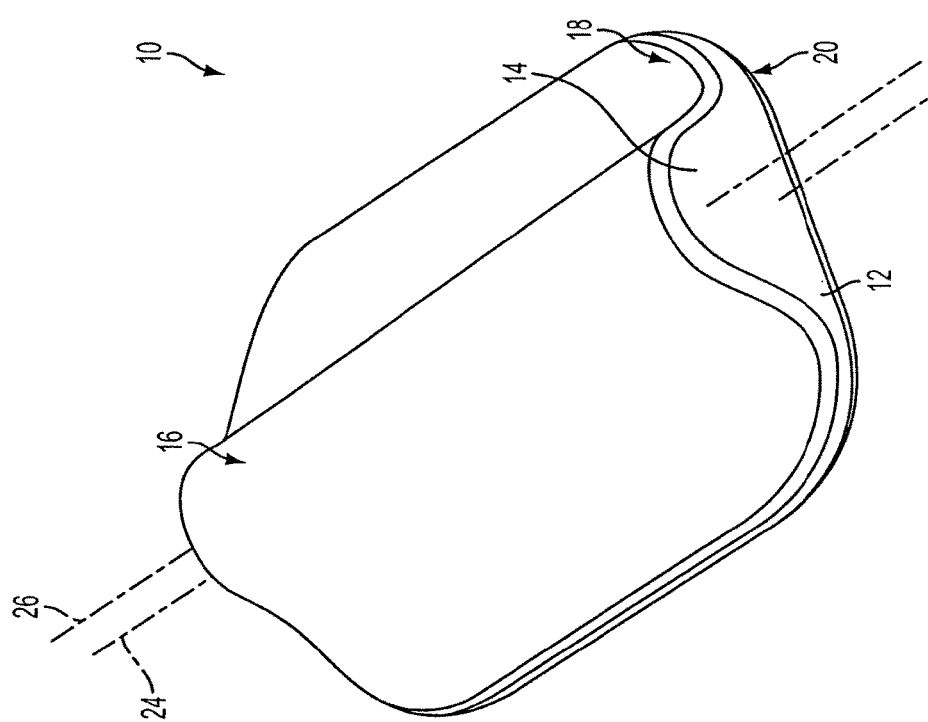
FIG. 1 is a perspective view of one embodiment of a device for preventing or reducing the severity of hemorrhoids.

The disclosed embodiments include devices, methods, and systems for use in a medical treatment to prevent or reduce the severity of hemorrhoids. These devices, methods and systems contemplate a proactive and inhibitive therapy.

Referring to FIGS. 1-12, embodiments include devices 10, 11, 13 formed by a base 12 having an extending raised portion 14, 15, 17 that, when positioned against a patient 49, applies pressure to a perianal region 60 adjacent to an external rectal venous plexus 62 to prevent and/or reduce the severity of hemorrhoids. Raised portion 14, 15, 17 may be formed of an elastic material so as to provide the pressure against areas of patient susceptible to hemorrhoids, as well as to allow for passage of a child's head through the birthing canal during childbirth, as is discussed below. In particular, raised portion 14, 15, 17 may form an elongated ridge defining a curved surface 16 raised up from an inner surface 18 of base 12, which further includes an opposing outer surface 20. In one embodiment, for example referring to FIG. 1, raised portion 14 comprises a partial, elongated cylindrical shape. In another embodiment, for example referring to FIGS. 10-11, raised portion 15 comprises a partial, elongated spherical shape. It should be noted that other combinations of linear, curved and spherical shapes may be utilized to form raised portion 14, 15, 17. Further, raised portion 14, 15, 17 may extend along all or only a portion of base 12. Additionally, all or a portion of curved surface 16 of raised portion 14 contacts perianal region 60 to provide pressure to oppose the distension of vascular tissue, such as external rectal venous plexus 62, outside of anal canal 64 and/or adjacent anal orifice 72 of patient 49. As such, in one embodiment, raised portion 14, 15, 17 may apply pressure primarily to prevent or reduce the severity of thrombosed external hemorrhoids.

In one embodiment, for example, raised portion 14 extends along longitudinal axis 26 a distance greater than the size of anal orifice 72, thereby substantially preventing raised portion 14 from entering anal canal 64. In another embodiment, raised portion 14 extends along longitudinal axis 26 a distance greater than the height of raised portion 14 relative to base 12. In another embodiment, curved surface 16 comprises a continuously curved surface extending from inner surface 18 of base 12 to an apex.

Optionally, for example referring to FIGS. 3-6, 8 and 12, devices 10, 13 may further include a plug portion 22, 23 extending from base 12 and raised portion 14, 17. Plug portion 22, 23 is shaped for insertion within anal canal 64 of patient 49. All or a portion of plug 22, 23 provides pressure to oppose the distension of vascular tissue, such as internal rectal venous plexus 68, within anal canal 64 and/or adjacent rectum 66. As such, plug portion 22, 23 may apply pressure primarily to prevent or reduce the severity of thrombosed internal hemorrhoids.

Thus, for example, while in place on the patient, devices 10, 11, 13 may either: entirely prevent the occurrence of hemorrhoids; may reduce the severity of hemorrhoids that do occur; and/or may reduce the severity of existing hemorrhoids. Further, these devices may apply pressure and prevent or reduce internal and/or external hemorrhoids, which often are associated with engorgement of the rectal venous plexus. Therefore device 10, 11, 13 may provide pressure to prevent or reduce the severity of distention of vascular tissue within all or a portion of the anorectal region of patient 49.

Figure 2:
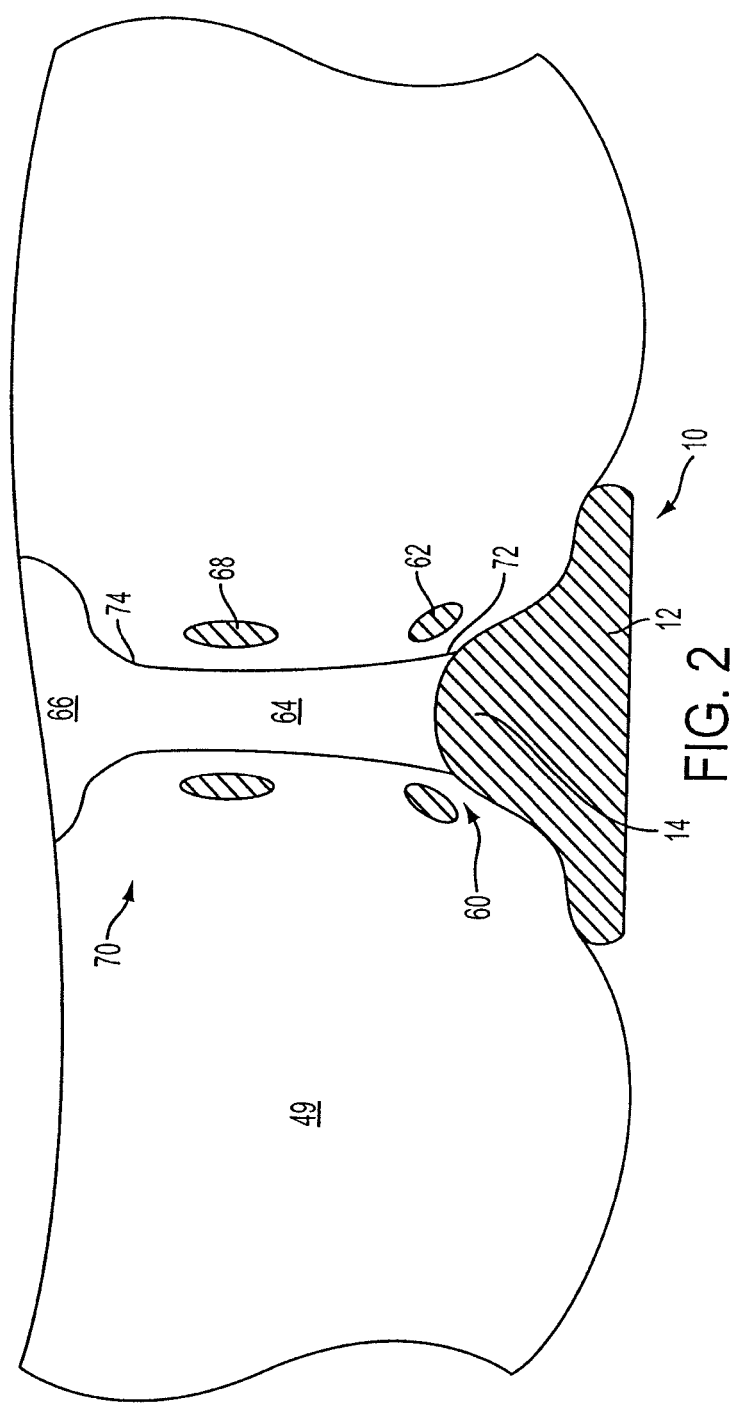
FIG. 2 is a partial axial cross-sectional view through the device of FIG. 1 while in position against a perianal region of a patient.
Figure 3:
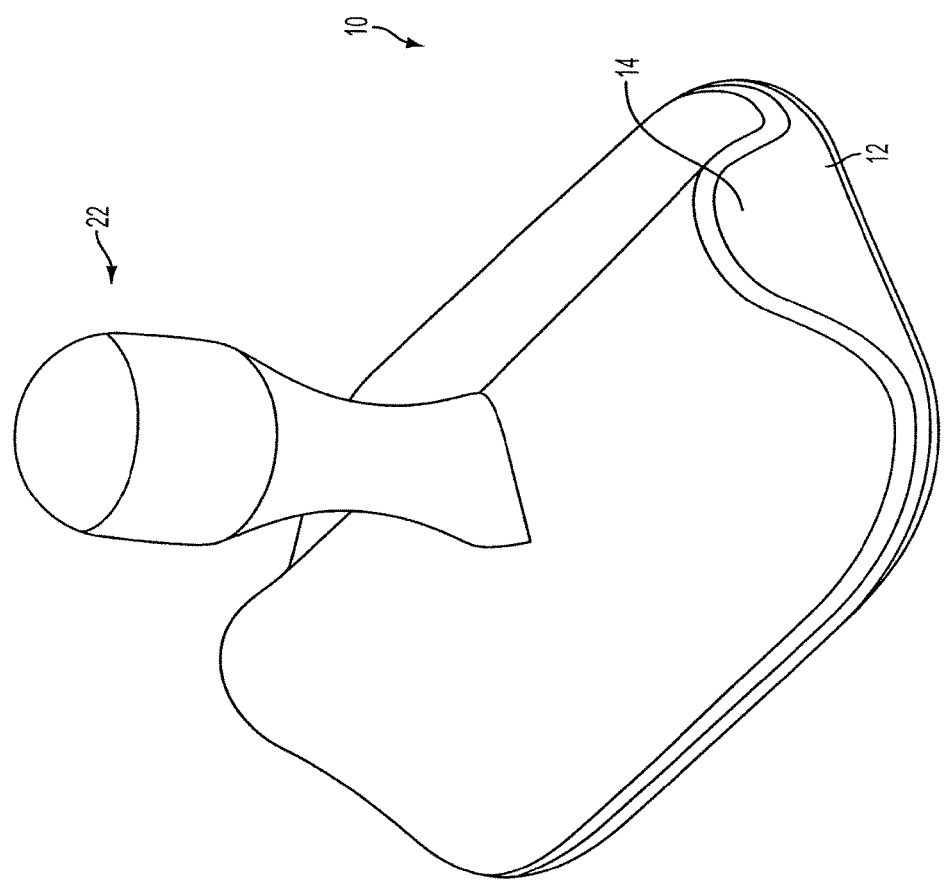
FIG. 3 is a perspective view of one embodiment of the device of FIG. 1 including a plug portion.
Figure 4:
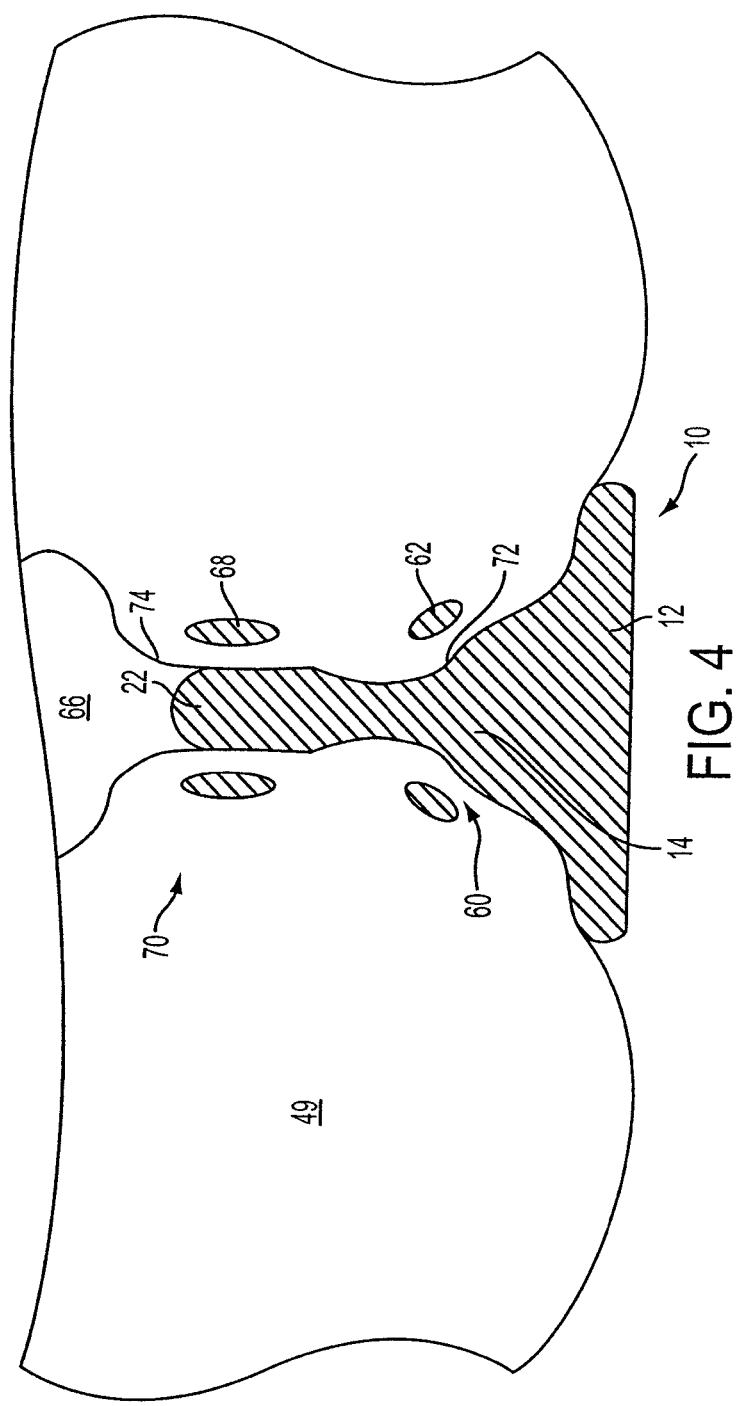
FIG. 4 is a partial axial cross-sectional view through the device of FIG. 3 while in position against the perianal region and within the anal canal of the patient.
Figure 8:
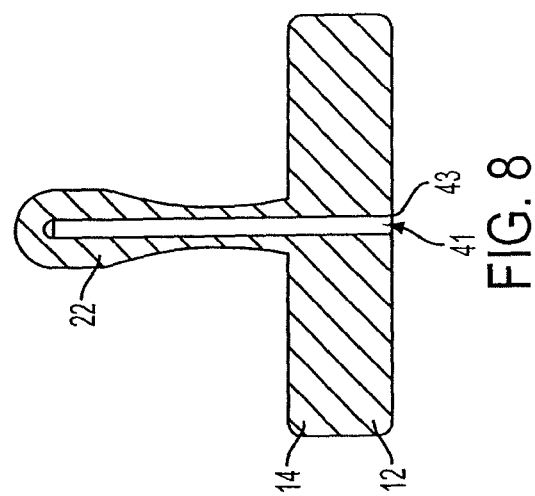
FIG. 8 is a cross-sectional view along line 8-8 of the device of FIG. 7.
Figure 7:
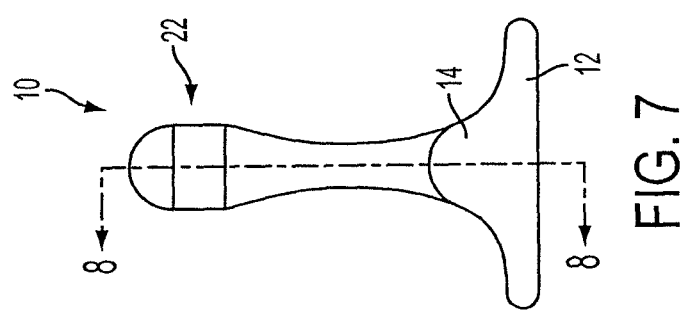
FIG. 7 is an end view of the device of FIG. 3.
Figure 9:
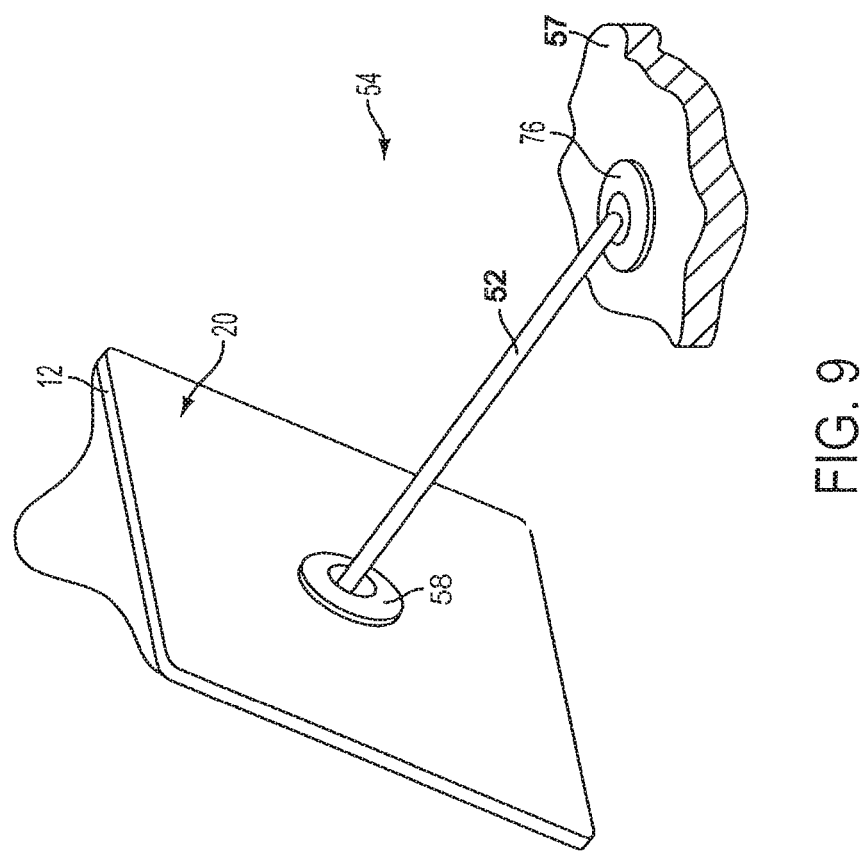
FIG. 9 is a bottom, perspective view of the device of FIG. 1 including a securing structure.

Referring to FIGS. 2 and 4, as used herein, the term "perianal region" 60 generally refers to an anal orifice 72 of patient 49 and the area near or around anal orifice 72. The term "anal orifice" 72, aka "anus," refers to the opening at the end of anal canal 64. The term "anal canal" 64 refers to the portion of the alimentary canal adjacent to the rectum 66, extending proximal to the dentate line 74 and ending at anal orifice 72. The term "rectum" 66 refers to the terminal portion of the large intestine, extending from the sigmoid colon to anal canal 64. The term "anorectal" region refers to the anal orifice, the anal canal and the rectum, or to the junction between these areas. The term "external rectal venous plexus" 62 refers to the portion of the venous system that forms external hemorrhoids, generally adjacent anal orifice 72. The term "internal rectal venous plexus" 68 refers to the portion of the venous system that forms internal hemorrhoids, generally located adjacent to the upper portion of anal canal 64 and adjacent to dentate line 74.

In one embodiment, for example, base 12 may extend, at least in part, along a longitudinal axis 24. Similarly, raised portion 14, 15, 17 may extend, at least in part, along a longitudinal axis 26. In an embodiment, longitudinal axis 26 associated with raised portion 14, 15, 17 is generally parallel to longitudinal axis 24 associated with base 12. Additionally, although shown in the described embodiments as lying in the same vertical plane, and thus having the same angular orientation within a horizontal plane, longitudinal axis 24 may have any angular orientation in the horizontal plane relative to longitudinal axis 26. Further, it should be noted that base 12 and/or raised portion 14, 15, 17 may have a generally curved and/or curvilinear shape, but such a shape may be considered to extend along the respective longitudinal axis 24 and/or longitudinal axis 26.

In some embodiments, plug 22, 23 may extend along a longitudinal axis 25, which may be at any angle 27 (FIG. 5) relative to base 12 and/or raised portion 14,17 or longitudinal axis 24 and/or longitudinal axis 26. In one embodiment, for example, longitudinal axis 25 may be substantially perpendicular to base 12 and/or raised portion 14, 17, or substantially perpendicular to longitudinal axis 24 and/or longitudinal axis 26. In another embodiment, for example, longitudinal axis 25 may be substantially acute relative to base 12 and/or raised portion 14, 17, or substantially acute relative to longitudinal axis 24 and/or longitudinal axis 26. Additionally, plug 22, 23 may be formed of an elastic or a deformable material such that in a first, unused state plug 22, 23 may extend along longitudinal axis 25, but in a second state corresponding to a use of the device, plug 22, 23 may extend along a longitudinal axis 29 having a different angle 27 relative to base 12 and/or raised portion 14, 17 or longitudinal axis 24 and/or longitudinal axis 26.

Plug 22,23 may include an expanded portion 31 for applying pressure to the internal anal canal anatomy of the patient, and a joining portion 33 for attaching expanded portion 31 to device 10,13. Expanded portion 31 may have any shape, but generally comprises a rounded end 35 to allow for easy insertion and a spherical and/or curvilinear body 37 to correspond with the internal anatomy of the anal canal of the patient. Similarly, joining portion 33 is generally a cylindrical and/or curved shape.

Figure 12:
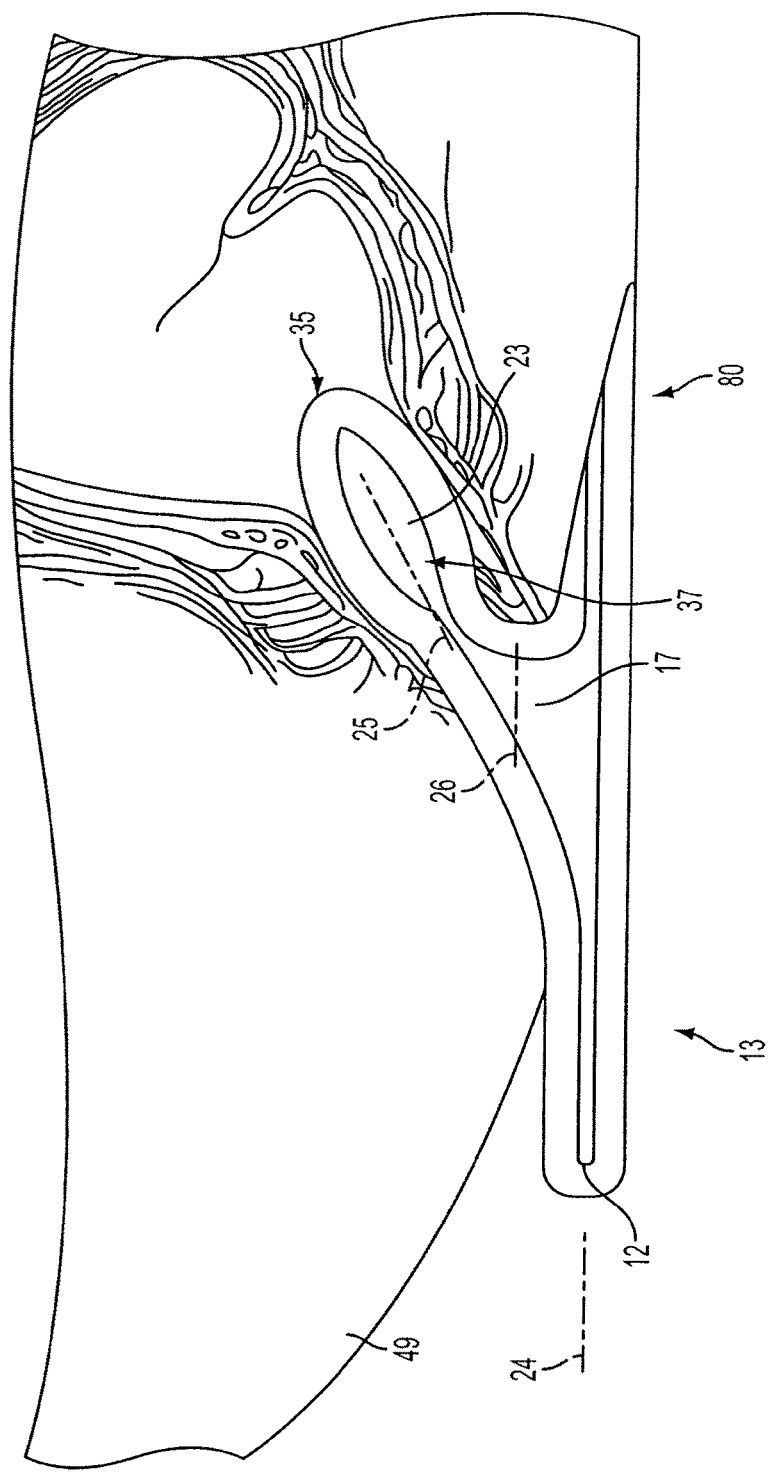
FIG. 12 is a partial cross sectional view of a patient including a side view of another embodiment of a device similar to that of FIG. 1, the device including an extended base portion for securing the device relative to the patient.

Although shown as having a generally rectangular-shaped perimeter 39 (FIG. 6), thereby providing a substantially constant width and length, base 12 may have any shape suitable for positioning against perianal region 60 of patient 49. For example, perimeter 39 may be shaped as an oval, a square, or any other combination of a curved, linear, and/or curvilinear shape. In one embodiment based on anatomical studies, for example, base 12 has a length extending along longitudinal axis 24 in the range of about 4 cm to about 8 cm and a width, perpendicular to the length, in the range of about 2 cm to about 6 cm. In another embodiment based on anatomical studies, for example, base 12 has a length extending along longitudinal axis 24 in the range of about 5 cm to about 7 cm and a width in the range of about 3 cm to about 5 cm. It should be noted, however, that base 12 may be sized to conform to a variety of sizes of perianal anatomy. Further, base 12, raised portion 14, 15, 17 and plug 22, 23, may be formed from a material so as to allow deformation to conform to the anatomy of the patient, or to provide space during childbirth, as is explained below. Such a material may be one or a combination of an elastic material and an inelastic material, as noted below. Further, base 12 may be sized to provide a mounting surface for securing mechanisms to attach device 10, 11, 13 to patient (see FIG. 15), to another securing point (FIG. 9), such as a table, or to stand upright such as on a table (FIG. 12). Such mounting and securing of the respective device will be discussed below in more detail.

Further, base 12 may include an internal cavity 41 (FIG. 8) having at least one open end 43, such as for receiving an insertion mechanism 44 (see FIG. 14) operable to control a position of the device during application of the device to the patient, as is discussed below in more detail. In some embodiments, internal cavity 41 may extend into raised portion 14, 15, 17 and/or plug 22, 23. Alternatively, rather than having internal cavity 41 and removable insertion mechanism 44, the described embodiments may include an attached insertion mechanism 45 (FIG. 11) connected to base 12 or some other portion of the respective device.

Referring to FIGS. 13-16, an additional embodiment includes device 19 to prevent or reduce the severity of hemorrhoids. Device 19 includes plug 47 extending directly from base 12, where plug 47 is similar to plug 22,23 discussed above. As such, plug 47 has a shape, which extends in a first direction parallel to longitudinal axis 25 and a second direction substantially perpendicular to axis 25, adapted to engage a hemorrhoidal, anorectal, venous, and/or perianal region of a patient 49 (FIG. 16). In particular, plug 47 may include an elongated bulbous body 37 having a first body portion 51 for engagement against perianal region 60, and, optionally, a second body portion 53 for insertion within anal canal 64 of patient 49 and engagement with anorectal region 30, or submucous space. Device 19 further includes an arm 32 extending along a flange longitudinal axis 34, where arm 32 is sized to limit movement of plug 47 relative to anal canal at least during engagement of plug 47 with the anorectal region 30. Additionally, plug 47 may be elastically deformable between a normal state 36 (e.g. FIG. 14) and a compressed state 38 (e.g. FIG. 16) to conform and apply pressure to anorectal region 70 of patient 49. For example, plug 47 may be formed from a rubber, an elastomer, a plastic, a silicone, or any other medically acceptable material as well as any other material capable of elastically deforming, as described below.

Device 19 prevents or reduces the severity of hemorrhoids by preventing portions of anorectal region 70 (as well as hemorrhoidal, venous, or vascular tissue) from protruding above or out from their typical location. In particular, base 12 is positioned against the outside of anal orifice 72, and plug 47 within anal canal 64, and thus device 19 applies pressure or prevents the distension or protrusion of hemorrhoidal, vascular, or anorectal tissue in these areas.

In one embodiment, rather than being applied to patient 49 to treat existing hemorrhoids, any one of devices 10,11, 13,19 may be proactively applied prior to the occurrence of hemorrhoids. By coming into contact with anal orifice 72, perianal region 60 and/or anorectal region 70, devices 10,11, 13,19 reduce blood flow or blood pressure in the areas of the body responsible for hemorrhoids. In addition, by coming into contact with these areas of the body, there is less room for protrusion or expansion of hemorrhoidal tissue. In either case, hemorrhoids may be prevented or their severity reduced through use of any one of devices 10,11,13,19. For example, hemorrhoids are characterized into 4 classes, with class 4 hemorrhoids being the worst case. In an example of reducing the severity of hemorrhoids, without treatment using device 10,11,13,19, patient 49 may experience class 2 hemorrhoids, whereas proactive treatment with device 10,11,13,17 results in class 1 hemorrhoids.

Figure 15:
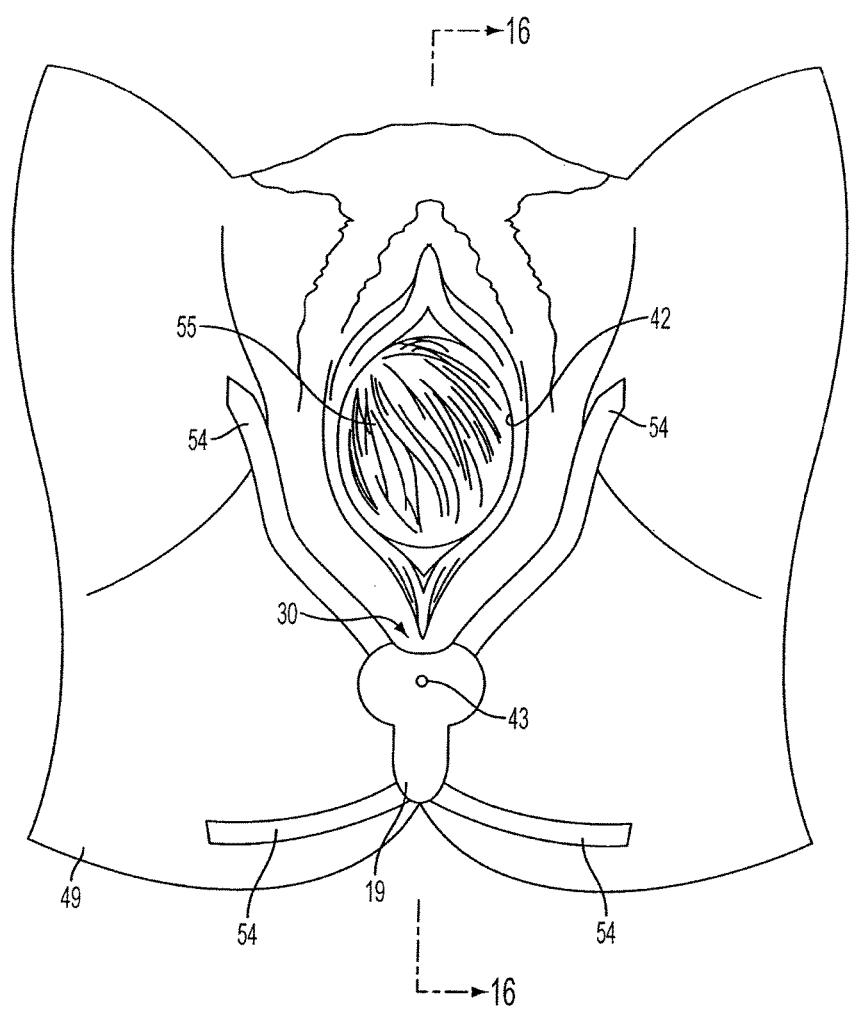
FIG. 15 is a bottom view of the device of FIG. 13 including an embodiment of a securing mechanism to attach the device to a patient during the childbirth process.

For instance, referring to FIGS. 12, 15 and 16, in one embodiment of a method to prevent or reduce the severity of hemorrhoids during childbirth, treatment of patient 49 with any of the described devices 10,11,13,19 includes positioning and securing raised portion 14, 15, 17 and/or plug 22,23,47 in an engagement position with perianal region 60 and/or anal canal 64 to respectively apply pressure to external rectal venous plexus 62 and/or internal rectal venous plexus 68 before or during a second stage of labor. For example, the second stage of labor may be defined as a state when the cervix of patient 49 approaches a dilation of about 10 cm, and when serious pushing begins. It should be noted, however, that device 10,11,13,19 may be applied to patient 49 at an earlier or later time. During this portion of the childbirth process, the head of a child 55 passing through the birthing canal pushes against the rectum 51 prior to passing through the opening of the vagina. The appearance of the baby's head at the vaginal opening, i.e. the vulvar ring 42, is often referred to as crowning. As the head of the child 55 pushes against anorectal region 70, the raised portion 14, 15, 17 and/or plug 22, 23, 47 changes from its normal state 36 to a compressed state 38. Compressed state 38 of raised portion 14, 15, 17 and/or plug 22, 23, 47 thereby provides additional space to allow for expansion of vulvar ring 42 and passage of the head of child 55.

Plug 47, as well as plugs 22, 23, is shaped to agree with the anorectal anatomy of the human body. In order to apply pressure in the engagement position to rectal hemorrhoidal plexus, which includes external rectal venous plexus 62 and/or internal rectal venous plexus 68, body 37 of plug 47 may extend a predetermined distance within anal canal 64. For example, in one embodiment based on anatomical studies, body 37 of plug 47 extends about 1 cm to about 6 cm inside the anal canal, while in another embodiment based on anatomical studies, body 37 extends about 2 cm to about 4 cm inside the anal canal. In the embodiment of plug 47 that includes second body portion 53, the bulbous or convex outer shape of plug 47 helps to secure the plug within anus 28. As such, plug 47 (as well as plugs 22 and 23) generally extend into anal canal 64 and apply pressure to an area adjacent to internal rectal venous plexus 68.

On the other hand, in the embodiments discussed above having raised portions 14, 15, 17 without plugs 22, 23, 47, the respective raised portions may have a height from their apex to the bottom of base 12 in the range of about 1 cm to about 3 cm, or in another embodiment from about 0.5 cm to about 2 cm, both ranges based on anatomical studies. Further, in one embodiment based on anatomical studies, curved surface 16 of raised portion 14 comprises a curve having a radius in the range of about 0.7 cm to about 1.5 cm, or in the range from about 0.9 cm to about 1.3 cm in another embodiment. As such, the respective raised portions 14, 15, 17 generally extend and apply pressure to an area adjacent to external rectal venous plexus 62, and raised portions have a radius of curvature sized to substantially prevent the apex of the respective raised portion from entering the anal canal of the patient.

Figure 14:
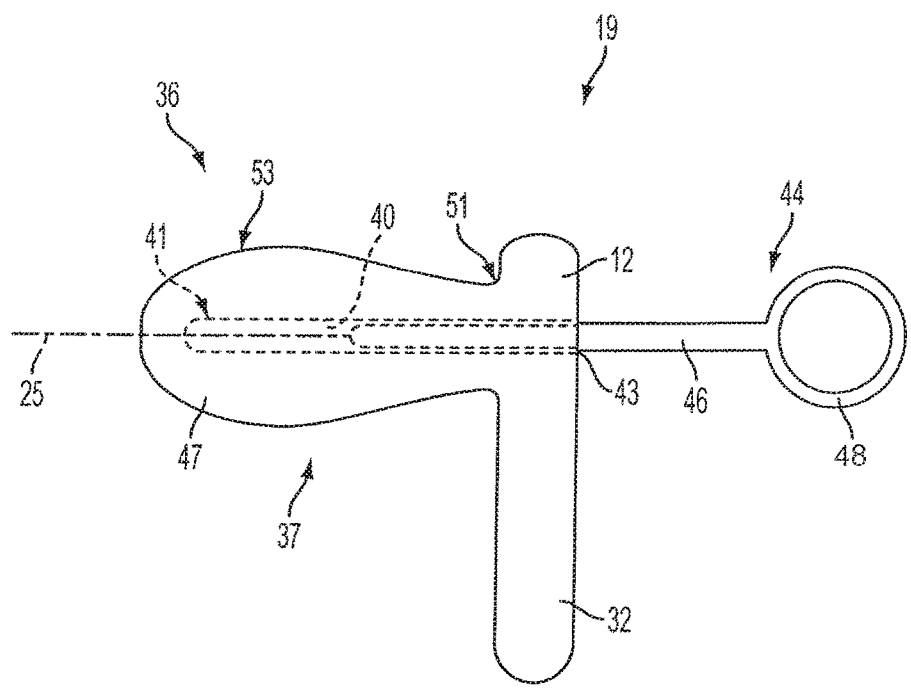
FIG. 14 is a side view of the device of FIG. 13, and further including an insertion mechanism.

Further, referring to FIG. 14, plug 47 may include an internal wall 40 that defines internal chamber 41 for receiving an insertion mechanism 44. For example, insertion mechanism 44 may include a rod 46 and a handle 48 or other easily grasped member that extends from device 19 and may be used to guide the placement and/or insertion of device 19 against and/or within anus 28. Chamber 41 and rod 46 are respectively sized for engagement and to allow removal of rod 46 from chamber 41 after placement of device 19. Additionally, chamber 41 may additionally provide additional space to increase the compressibility of device 19 in compressed state 38.

Figure 10:
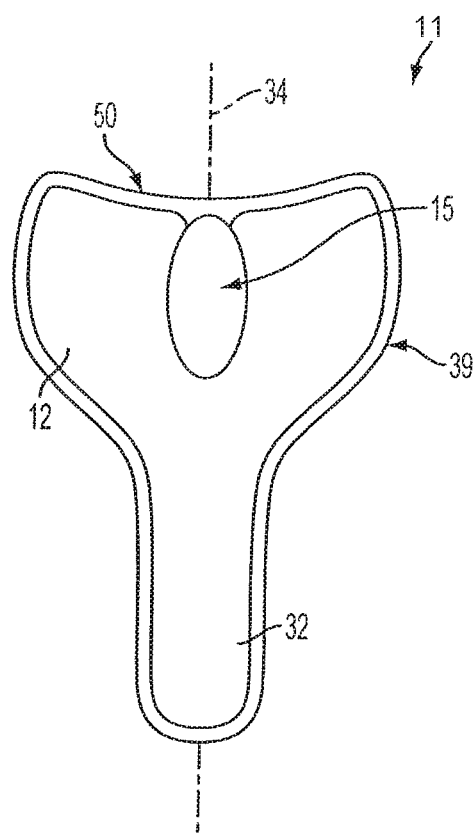
FIG. 10 is a front view of another embodiment, similar to FIG. 1, of a device for preventing or reducing the severity of hemorrhoids.
Figure 11:
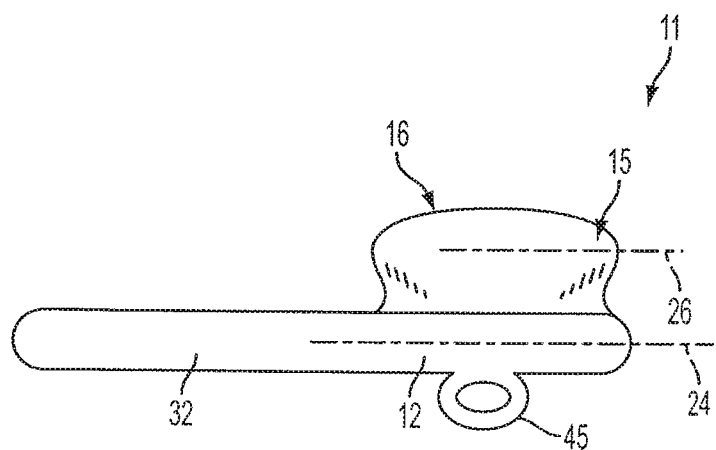
FIG. 11 is a side view of the device of FIG. 10, including an integral insertion mechanism.

Alternatively, referring to FIGS. 10-11, device 11 includes insertion mechanism 45 that may be fixed to, and/or integrally-formed with, device 11. For example, insertion mechanism 45 may include a tab, a ring or any other structure extending from base 12 that allows device 11 to be held and positioned relative to patient 49. Further, in this embodiment which is intended for placement against external rectal venous plexus 62, device 11 is positioned outside of but adjacent to anal orifice 72. Further, in one embodiment, the body of raised portion 15 extends further in a first direction along longitudinal axis 24 of base 12 than in a second direction away from the base, such as a direction corresponding to a height of raised portion 15.

Referring back to FIGS. 13-15, base 12 includes perimeter edge 39, which in this embodiment includes a concave portion 50 centered about flange longitudinal axis 34. This relative positioning aligns concave portion 50 with the vaginal opening of patient 49, thereby providing access for performing an episiotomy, if necessary, without having to remove the device. Further, as discussed above, base 12 may include an arm member 32, which is sized to fit between the buttocks of patient 49 to aid in securing device 10.

Further, base 12 may extend substantially within a plane parallel to longitudinal axis 24. Base 12 may be formed from an elastic material that allows for bending and/or compression. Alternatively, base 12 may have a predefined curved or curvilinear shape to conform to the perianal or anorectal anatomy of patient 49. For example, referring to FIG. 1, base 12 includes inner surface 18 having a curved shape that transitions into raised portion 14. As such, inner surface 18 is shaped to conform to the portion of perianal region 60 outside of anal orifice 72, e.g. the region transitioning from the buttocks to the anal orifice.

Additionally, any one of the respective devices 10,11,13, 19 may further include a securing mechanism 54 (FIGS. 9 and 15) to fix the respective device to patient 49. For example, securing mechanism 54 may include tape, glue or any other removable mechanism for fastening the respective device relative to patient 49. In one embodiment, referring to FIG. 15, fastening mechanism 54 comprises tape. In another embodiment, referring to FIG. 9, fastening mechanism 54 includes a leg member 52 securing a portion of the respective device, such as base 12, to a foundation 57, such as a table. Leg 52 may be fixed to base 12 through a first connecting member 58, and secured to foundation 57 through a second connecting member 76. For example, first and second connecting members 58, 76 may include one or a combination of mechanisms such as a snap ring, a ball joint, a threaded connection, etc. Leg 52 may be formed of a relatively rigid and/or elastic material to provide resistance to relative movement between base 12 and foundation 57, thereby providing pressure to the hemorrhoidal regions through the respective device.

Figure 13:
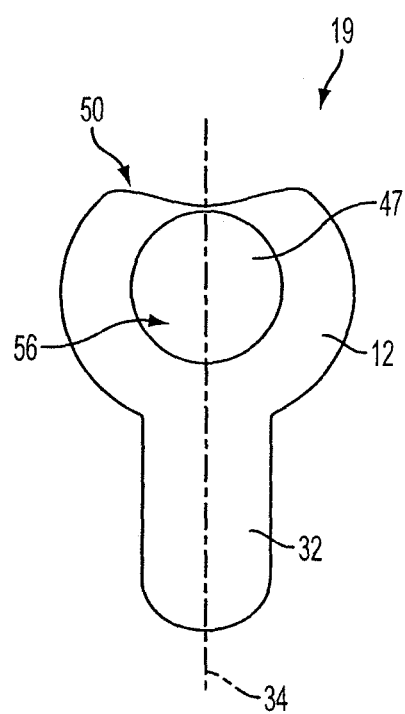
FIG. 13 is front view of another embodiment of a device, similar to FIG. 10, and including a concave perimeter portion to allow for an episiotomy.

Further, referring to FIG. 13, device 19 may include a lubrication layer 56 disposed on the surface of plug 47 to ease the placement against or insertion within anus 28. For example, lubrication layer 56 may include a silicone, petroleum jelly, baby oil, or any other biomedically acceptable lubricant that reduces friction between plug 47 and patient 49. It should be noted that lubrication layer 56 may be provided on plugs 22 and 23, as well as on raised portions 14, 15 and 17.

Further, in the embodiment of FIG. 12, device 13 may be essentially similar to device 10, but plug 23 extends about longitudinal axis 25 oblique to the longitudinal axis 24 and/or base 12. As such, base 12 allows device 13 to stand on a delivery table, and a portion 80 of base 12 is captured between the top of the delivery table and the body of patient 49, thereby providing a securing mechanism for fixing device 13 relative to patient 49. Further, in this embodiment, portion 80 of base 12 may define a ramp-like portion that is thinner at its edge, thereby providing a comfortable transition onto device 13 for patient 49.

Thus, devices 10, 11, 13, 19 come into contact with and/or are inserted into: the anus, anal canal, anorectal region, and/or perianal region. Such contact produces an engagement position that applies pressure to these areas, resultingly decreasing the pooling of blood and/or anorectal pressure, and preventing the distortion and/or enlargement of anorectal, venous, and/or hemorrhoidal tissue. In other words, these devices engage at least one of these 4 areas and, as a result, prevent the enlargement of anorectal (the anus and about 5 cm inside the rectum, which includes both the internal and external hemorrhoids), venous (veins responsible for swelling into hemorrhoids), and anorectal tissue (any skin that would swell or protrude in this area, namely the tissue that lies above the veins).

While the various disclosed embodiments have been illustrated and described, it will be clear that the subject matter of this document is not limited to these embodiments only. Any feature of one described embodiment may be incorporated into another described embodiment. Further, numerous other modifications, changes, variations, substitutions and equivalents will be apparent to those skilled in the art without departing from the spirit and scope of the disclosed embodiments as described in the claims.

What is claimed is:

1. A device for preventing or reducing a severity of external hemorrhoids in a patient during childbirth, an anus of the patient being defined by an anal orifice, the device comprising:

a base having a first longitudinal axis, a first side, a second side, and a surface extending from the first side of the base in a first direction corresponding to a height of the surface, the surface having a second longitudinal axis with a constant angular orientation relative to the first longitudinal axis, the base comprising an opening to a cavity at the second side of the base extending in the first direction toward the height of the surface, the surface and anatomically configured to contact only the perianal region, not substantially enter an anal canal of the patient, and not substantially interfere with a birthing canal of the patient during childbirth; and a positioning member extending from the second side of the base in a second direction away from the first side, comprising an insertion mechanism attachable to the device comprising a distal end configured to engage with the opening and the cavity at the second side of the base and a handle at a proximal end, the insertion mechanism operable in response to insertion into the cavity to control a position of the device with the handle during application of the device to the patient, the handle including a substantially rigid structure configured for gripping by a user to position and hold the device against the anal orifice of the patient.

2. The device of claim 1, wherein the device comprises a perimeter edge having a concave portion alignable with a vagina of the patient.

3. The device of claim 1, wherein the surface comprises a continuously curved surface extending outwardly from the base.

4. The device of claim 3, wherein the surface comprises a convex, curved surface having an apex, wherein the convex, curved surface has a radius of curvature configured to substantially prevent the apex from entering the anal canal of the patient.

5. The device of claim 4, wherein a height from the bottom of the base to the apex is in the range of about 1 cm. to about 3 cm.

6. The device of claim 1, further comprising a securing mechanism attachable to the device, the securing mechanism adapted to fix the device relative to the patient.

7. The device of claim 1, wherein the handle comprises a ring.

8. The device of claim 1, wherein the handle comprises a tab.

9. The device of claim 1, wherein the insertion mechanism comprises a rod.

10. The device of claim 1, wherein the cavity comprises opposing cavity surfaces at the second side of the base.

11. The device of claim 1, wherein a location in the base of the opening to the cavity is between a first portion of the second side of the base and a second portion of the second side of the base, the first and second portions being substantially symmetrical to each other on either side of the location of the opening.

12. A device for preventing or reducing a severity of external hemorrhoids in a perianal region of a patient during childbirth, comprising:

a means external to an anal canal of the patient, the means comprising a base having a first longitudinal axis and first and second sides, and a continuously curved surface extending from the first side of the base, the surface having a second longitudinal axis with a constant angular orientation relative to the first longitudinal axis, and an opening to a cavity at the second side of the base extending in a direction toward a height of the continuously curved surface;

a positioning member extending from the second side of the base in a direction away from the first side, comprising an insertion mechanism attachable to the device comprising a distal end configured to engage with the opening and the cavity at the second side of the base and a handle at a proximal end, the insertion mechanism operable in response to insertion into the cavity to control a position of the device with the handle during application of the device to the patient, the handle configured for gripping by a user to guide placement of the surface against an anal orifice of the patient, the means configured to apply pressure to only the perianal region of the patient to apply pressure to an external rectal venous plexus without interfering with a birthing canal of the patient during childbirth; and an external means for securing the means for applying pressure to the patient to maintain engagement with the perianal region, without interfering with the birthing canal during childbirth, the external means being separate from the positioning member.

13. The device of claim 12, wherein the surface is configured to contact substantially only the perianal region of the patient.

14. The device of claim 13, wherein the height of the continuously curved surface comprises a convex, curved surface having an apex, wherein the convex, curved surface has a radius of curvature configured to substantially prevent the apex from entering the anal canal of the patient.

15. The device of claim 14, wherein the base includes a shaped portion at a perimeter edge thereof to face a vagina of the patient during childbirth.

16. The device of claim 13, wherein the external means for securing includes a securing mechanism attachable to the base, the securing mechanism adapted to fix the surface relative to the patient.

17. The device of claim 12, wherein the means for securing comprises an adhesive applied to the outside of the patient.

18. The device of claim 12, wherein the means for securing includes adhesive tape applied to the outside of the patient.

19. The device of claim 12, wherein the handle comprises a ring.

20. The device of claim 12, wherein the handle comprises a tab.

21. The device of claim 12, wherein the insertion mechanism comprises a rod.

22. The device of claim 12, wherein the cavity comprises opposing cavity surfaces at the second side of the base.

23. The device of claim 12, wherein a location in the base of the opening to the cavity is between a first portion of the second side of the base and a second portion of the second side of the base, the first and second portions being substantially symmetrical to each other on either side of the location of the opening.

24. A device for preventing or reducing a severity of hemorrhoids in a perianal region of a patient during childbirth, an anus of the patient being defined by an anal orifice, comprising:

a body including a base having an inner surface, an opposing outer surface, a first longitudinal axis, and a contact surface extending from the inner surface of the base, the contact surface having a second longitudinal axis with a constant angular orientation relative to the first longitudinal axis, the contact surface configured to contact only the perianal region, and to not substantially enter the anal canal, and to not substantially interfere with the birthing canal of the patient during childbirth, the base further comprising an opening to a cavity at the opposing outer surface extending in a direction toward a height of the contact surface;

a positioning member extending from the opposing outer surface of the base in a direction away from the inner surface, comprising an insertion mechanism attachable to the device comprising a distal end configured to engage with the opening and the cavity at the opposing outer surface of the base and a handle at a proximal end, the insertion mechanism operable in response to insertion into the cavity to control a position of the device with the handle during application of the device to the patient, the handle configured for gripping by a user to position and hold the device against the anal orifice of the patient; and a securement member to hold the contact surface against the perianal region to thereby prevent or reduce a distention or a protrusion of hemorrhoid, venous or vascular tissue adjacent the anal orifice, the securement member being separate from the positioning member.

25. The device of claim 24, wherein the securement member extends along a third axis, the third axis being substantially transverse to the second longitudinal axis.

26. The device of claim 24, wherein the insertion mechanism comprises a rod.

27. The device of claim 24, wherein the cavity comprises opposing cavity surfaces at the opposing outer surface of the base.

28. The device of claim 24, wherein a location in the base of the opening to the cavity is between a first portion of the opposing outer surface of the base and a second portion of the opposing outer surface of the base, the first and second portions being substantially symmetrical to each other on either side of the location of the opening.

29. A device for preventing or reducing a severity of hemorrhoids in a perianal region of a patient during childbirth, the device comprising:

a body having an inner surface and a pair of opposed exterior surfaces extending continuously from the inner surface, the pair of opposed exterior surfaces joined to each other at an apex, and an opening to a cavity at the inner surface of the body extending in a direction toward the apex, the apex being configured to engage only the perianal region posterior to the vaginal opening to prevent entry into the anal canal and the pair of opposed exterior surfaces being configured to engage at least a portion of the perianal region transitioning from an anal orifice of the patient to a buttocks of the patient; and a positioning member extending from the inner surface of the body in a constant direction away from the apex, comprising an insertion mechanism attachable to the device comprising a distal end configured to engage with the opening and the cavity at the inner surface of the body and a handle at a proximal end, the insertion mechanism operable in response to insertion into the cavity to control a position of the device with the handle during application of the device to the patient, the handle configured for gripping by a user to position and hold the device against the anal orifice of the patient.

30. The device of claim 29, wherein the apex is curved.

31. The device of claim 30, wherein the apex comprises a partial, elongated cylindrical shape.

32. The device of claim 29, wherein the pair of opposed exterior surfaces extend laterally away from the apex to engage at least a portion of the perianal region transitioning from the anal orifice to the buttocks laterally adjacent the anal orifice.

33. The device of claim 29, further including at least one elongated securing member attached to the body and the apex defining a longitudinal axis, the securing member extending substantially transverse to the longitudinal axis.

34. The device of claim 33, wherein the elongated securing member includes an adhesive portion for securing to the patient.

35. The device of claim 33, further including at least two elongated securing members, each securing member extending away from the body substantially transverse to the longitudinal axis.

36. The device of claim 29, wherein the insertion mechanism comprises a rod.

37. The device of claim 29, wherein:
the cavity comprises opposing cavity surfaces at the inner surface of the body,
a location in the body of the opening to the cavity is between a first portion of the inner surface of the body including a first cavity surface of the opposing cavity surfaces and a second portion of the inner surface of the body including a second cavity surface of the opposing cavity surfaces, and
the first and second portions are substantially symmetrical to each other on either side of the location of the opening.

* * * * *